US010479773B2

(12) United States Patent
Chheda et al.

(10) Patent No.: US 10,479,773 B2
(45) Date of Patent: Nov. 19, 2019

(54) LIGNIN-BASED SOLVENTS AND METHODS FOR THEIR PREPARATION

(71) Applicant: SHELL OIL COMPANY, Houston, TX (US)

(72) Inventors: Juben Nemchand Chheda, Houston, TX (US); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/173,683

(22) PCT Filed: May 2, 2017

(86) PCT No.: PCT/US2017/030522
§ 371 (c)(1),
(2) Date: Oct. 29, 2018

(87) PCT Pub. No.: WO2017/192498
PCT Pub. Date: Nov. 9, 2017

(65) Prior Publication Data
US 2019/0144409 A1    May 16, 2019

Related U.S. Application Data

(60) Provisional application No. 62/331,197, filed on May 3, 2016.

(51) Int. Cl.
C07D 307/50 (2006.01)
C07G 1/00 (2011.01)

(52) U.S. Cl.
CPC .............. *C07D 307/50* (2013.01); *C07G 1/00* (2013.01)

(58) Field of Classification Search
CPC ..................................................... C07D 307/50
USPC ......................................................... 549/483
See application file for complete search history.

(56) References Cited

U.S. PATENT DOCUMENTS

| | | |
|---|---|---|
| 2,078,241 A | 4/1937 | Fulmer et al. |
| 2,536,732 A | 1/1951 | Dunlop |
| 3,549,319 A | 12/1970 | Wilson et al. |
| 4,409,032 A | 10/1983 | Paszner et al. |
| 4,461,648 A | 7/1984 | Foody |
| 4,533,743 A | 8/1985 | Medeiros et al. |
| 5,536,325 A | 7/1996 | Brink |
| 5,789,210 A | 8/1998 | Ho et al. |
| 5,820,687 A | 10/1998 | Farone et al. |
| 6,475,768 B1 | 11/2002 | Otero et al. |
| 7,741,084 B2 | 6/2010 | Viitanen et al. |
| 7,741,119 B2 | 6/2010 | Viitanen et al. |
| 7,781,191 B2 | 8/2010 | Dunson, Jr. et al. |
| 8,168,807 B2 | 5/2012 | Wabnitz et al. |
| 8,466,242 B2 | 6/2013 | Geremia et al. |
| 10,005,749 B2 * | 6/2018 | Chheda ............... C07D 307/50 |
| 10,093,639 B2 * | 10/2018 | Chheda ............... C07D 307/50 |
| 10,138,218 B2 * | 11/2018 | Chheda ............... C07D 307/46 |
| 2003/0162271 A1 | 8/2003 | Zhang et al. |
| 2009/0061490 A1 | 3/2009 | Edwards et al. |
| 2010/0019191 A1 | 1/2010 | Hoffer et al. |
| 2010/0312028 A1 | 12/2010 | Olson et al. |
| 2012/0107887 A1 | 5/2012 | Chheda et al. |
| 2012/0122152 A1 | 5/2012 | Blackboum et al. |
| 2012/0157697 A1 | 6/2012 | Burket et al. |
| 2012/0302765 A1 | 11/2012 | Dumesic et al. |
| 2013/0295629 A1 | 11/2013 | Weider et al. |
| 2014/0018555 A1 | 1/2014 | De Vries et al. |
| 2014/0107355 A1 | 4/2014 | Dumesic et al. |

FOREIGN PATENT DOCUMENTS

| | | |
|---|---|---|
| EP | 1727890 A1 | 12/2006 |
| WO | 9742307 A1 | 11/1997 |
| WO | 2006096130 A1 | 9/2006 |
| WO | 2007009463 A2 | 1/2007 |
| WO | 2007028811 A1 | 3/2007 |
| WO | 2007136762 A2 | 11/2007 |

(Continued)

OTHER PUBLICATIONS

International Search Report and Written Opinion received for PCT Patent Application No. PCT/US2017/030522, dated Jun. 27, 2017, 9 pages.
International Search Report and Written Opinion received for PCT Patent Application No. PCT/US2015/44994, dated Nov. 2, 2015, 8 pages.
International Search Report and Written Opinion received for PCT Patent Application No. PCT/US2015/44988, dated Nov. 23, 2015, 7 pages.
International Search Report and Written Opinion received for PCT Patent Application No. PCT/US2015/44983, dated Nov. 2, 2015, 7 pages.
International Search Report and Written Opinion received for PCT Patent Application No. PCT/US2015/44981, dated Nov. 2, 2015, 8 pages.

(Continued)

*Primary Examiner* — Charanjit Aulakh

(57) ABSTRACT

Implementations of the disclosed subject matter provide a process for converting biomass into furfural. The process may include subjecting a pentosan-containing biomass material to an acid catalyzed digestion process in a digestion vessel to produce a digested product stream comprising C5-carbohydrates and solids comprising cellulose. The digested product stream may be separated into a liquid product stream and a solid product stream comprising lignin and cellulose. The solids product stream may be contacted with water and an organic solvent, thereby converting at least part of the lignin to a phenolic solvent. The C5-carbohydrate in the liquid product stream may be subjected to a dehydration reaction in the presence of an acid catalyst and a biphasic mixture comprising an aqueous phase and a water-immiscible organic phase, wherein the water-immiscible organic phase includes at least a portion of the phenolic solvent, to produce furfural or a furan derivative.

10 Claims, 3 Drawing Sheets

(56) References Cited

FOREIGN PATENT DOCUMENTS

| WO | 2008119082 A2 | 10/2008 |
| --- | --- | --- |
| WO | 2009109631 A1 | 9/2009 |
| WO | 2012041990 A1 | 4/2012 |
| WO | 2014159887 A1 | 10/2014 |
| WO | 2016025673 A1 | 2/2016 |
| WO | 2016025674 A1 | 2/2016 |
| WO | 2016025677 A1 | 2/2016 |
| WO | 2016025678 A1 | 2/2016 |
| WO | 2016025679 A1 | 2/2016 |

OTHER PUBLICATIONS

Lange et al., "Furfural-A Promising Platform for Lignocellulosic Biofuels", ChemSuschem, vol. 5, Issue No. 1, Jan. 9, 2012, pp. 150-166.

Kumar et al., "Methods for Pretreatment of Lignocellulosic Biomass for Efficient Hydrolysis and Biofuel Production", Industrial & Engineering Chemical Research, vol. 48, Issue No. 8, Mar. 20, 2009, pp. 3713-3729, XP002670851.

Galbe et al., "A review of the production of ethanol from softwood", Appl Microbiol Biotechnol, vol. 59, Jul. 17, 2002, pp. 618-628.

Ong, "Conversion of Lignocellulosic Biomass to Fuel Ethanol—A Brief Review", The Planter, vol. 80, Issue No. 941, Aug. 2004, pp. 517-524.

Lavarack et al., "The Acid Hydrolysis of Sugarcane Bagasse Hemicellulose to Produce Xylose, arabinose, glucose and Other Products", Biomass and Bioenergy, vol. 23, May 22, 2002, pp. 367-380.

Yang et al., "One-Step Catalytic Transformation of Carbohydrates and Cellulosic Biomass to 2,5-Dimethyltetrahydrofuran for Liquid Fuels", ChemSusChem, vol. 3, Issue No. 5, May 25, 2010, pp. 597-603.

Brown et al., "Fast Pyrolysis and Bio-Oil Upgrading", Biomass-to-Diesel Workshop, Pacific Northwest National Laboratory Richland, Sep. 5-6, 2006, pp. 1-46.

Mosier et al., "Features of Promising Technologies for Pretreatment of Lignocellulosic Biomass", Bioresource Technology, vol. 96, 2005, pp. 673-686.

Holtzapple et al., "The Ammonia Freeze Explosion (AFEX) Process—A Practical Lignocellulose Pretreatment", Applied Biochemistry and Biotechnology, vol. 28/29, 1991, pp. 59-74.

Moller, "Cell Wall Saccharification", Outputs from the EPOBIO Project, Nov. 2006, 69 pages.

Dumesic et al., "Conversion of Hemicellulose to Furfural and Levulinic Acid using Biphasic Reactors with Alkylphenol Solvents", ChemSusChem, vol. 5, Issue No. 2, Feb. 2012, pp. 383-387.

Shang-Xing et al., "Study on Dilute-acid Pretreatment of Corn Stalk", Chemistry and Industry of Forest Products, vol. 29, Issue No. 2, Dec. 31, 2009, pp. 27-32.(English Abstract Available).

Weingarten et al., "Design of Solid Acid Catalysts for Aqueous-phase Dehydration of Carbohydrates: The Role of Lewis and Bronsted Acid Sites", Journal of Catalysis, vol. 279, Issue No. 1, Apr. 24, 2011, pp. 174-182.

Cai et al., "Integrated Furfural Production as a Renewable Fuel and Chemical Platform From Lignocellulosic Biomass", Chemical Technology and Biotechnology, Jan. 2014, vol. 89, Issue No. 1, pp. 2-10, XP002776415.

Mansilla et al., "Acid-catalysed Hydrolysis of Rice Hull: Evaluation of Furfural Production", Bioresource Technology, vol. 66, Issue No. 3, Dec. 1998, pp. 189-193.

Molina et al., "Cyclopentyl Methyl Ether: a Green Co-solvent for the Selective Dehydration of Lignocellulosic Pentoses to Furfural", Bioresource Technology, vol. 126, Dec. 2012, pp. 321-327.

Moreau et al., "Selective Preparation of Furfural From Xylose Over Microporous Solid Acid Catalysts", Industrial Crops and Products, vol. 7, Issue No. 2-3, Jan. 1998, pp. 95-99, XP002646354.

Ordomsky et al., "Biphasic Single-reactor Process for Dehydration of Xylose and Hydrogenation of Produced Furfural", Applied Catalysis A: General, vol. 451, Jan. 31, 2013, pp. 6-13.

"New IUPAC Notation", Periodic Table of the Elements, Chemical and Engineering News, vol. 63, Issue No. 5, Feb. 4, 1985, p. 27.

Lide et al., "Periodic Table of the Elements", CRC Handbook of Chemistry and Physics, Internet Version 2005, <http://www.hbcpnetbase.com>, CRC Press, Boca Raton, FL, 2005, 3 pages.

* cited by examiner

LIGNIN-BASED SOLVENTS AND METHODS FOR THEIR PREPARATION

CROSS REFERENCE TO RELATED APPLICATIONS

This is a national stage application of International Application No. PCT/US2017/030522, filed 2 May 2017, which claims benefit of priority to U.S. Patent Application No. 62/331,197, filed 3 May 2016.

TECHNICAL FIELD OF THE INVENTION

The present invention relates to novel processes for the preparation of furfural from C5 sugars. More specifically, the invention pertains to a process for the conversion of biomass to furfural and the preparation of lignin-based solvents used in the process for converting biomass to furfural.

BACKGROUND

Lignocellulosic biomass is viewed as an abundant renewable resource for fuels and chemicals due to the presence of sugars in the cell walls of plants. More than 50% of the organic carbon on the earth's surface is contained in plants. This lignocellulosic biomass is comprised of hemicelluloses, cellulose and smaller portions of lignin and protein. Cellulose is a polymer comprised mostly of condensation polymerized glucose and hemicellulose is a precursor to pentose sugars, mostly xylose. These sugars can easily be converted into fuels and valuable components, provided they can be liberated from the cell walls and polymers that contain them. However, plant cell walls have evolved considerable resistance to microbial, mechanical or chemical breakdown to yield component sugars. A number of approaches to overcome this recalcitrance have been performed and the breakdown of these polymers into sugars, saccharification, has a long history. During such breakdown and/or saccharification, monomeric and oligomeric pentoses contained in the cell walls are released and can be subjected to acid-catalyzed dehydration to provide furfural, an important bio-based intermediate in the manufacture of fuel and chemicals, as reviewed by J. P. Lange, E. van der Heide, J. van Buijtenen, R. J. Price, ChemSusChem 2012, 5, 150-166.

US 20140018555 describes a process for producing furfural from lignocellulose-comprising biomass is disclosed. The biomass is slurried in water and optionally an acid, subjected to hydrolysis, and then subjected to a solid/liquid separation to yield at least an aqueous fraction comprising C5 and C6 sugars and a solid fraction comprising cellulose and lignin. Furfural is obtained by adding an organic solvent to the aqueous fraction, heating at 120-220° C. for a sufficient time to form furfural, cooling, and separating an organic phase comprising at least part of the furfural from an aqueous phase. As suitable organic solvents water miscible and water immiscible organic solvents are suggested. However, the process of US 20140018555 requires a continuous supply of organic solvent, which is undesired when the process is operated at remote locations. There is a need for improving the efficiency of the process by reducing the demand for organic solvent to be provided to the process.

Dumesic et al, (Elif I. Gurbuz, Stephanie G. Wettstein, and James A. Dumesic, Conversion of Hemicellulose to Furfural and Levulinic Acid using Biphasic Reactors with Alkylphenol Solvents, ChemSusChem 2012, 385-387) reported the acid-catalysed dehydration of xylose to furfural using a bi-phasic medium based on water and lignin-derived solvent (LDS). The LDS was shown to be a powerful extractant for furfural and can be made from the lignocellulose, avoiding thereby the need for external solvent. In Dumesic, the lignin-derived solvent (LDS) was derived from poplar wood using hot-compressed water under moderate hydrogen pressure utilizing a metal catalyst, followed by extraction from the aqueous phase using diethyl ether (DEE) to obtain a mixture of propyl guaiacol (PG), propyl syringol (PS), guaiacyl propanol and syringyl propanol. The final LDS mixture was obtained by evaporating the DEE solvent, followed by the removal of guaiacyl propanol and syringyl propanol from the mixture by extraction with water, leaving a hydrophobic organic phase composed of PS and PG in a 4:1 mass ratio. This process taught by Dumesic requires the use of solid precious metal catalyst in the presence of solid biomass to produce the LDS component. As such, the process taught by Dumesic is complex and expensive to separate the metal catalyst from solid biomass after the reaction. Also, the impurities in biomass may shorten the life of the catalyst in Dumesic. Further, in Dumesic, the LDS component needs to be further extracted via solvent leading to complex separations to produce the LDS component for use in the reaction for furfural production. In contrast, the presently disclosed subject matter provides for separation of the lignin from the pre-treated biomass by solvent treatment without the need for any solid metal catalyst, thereby simplifying the process steps to produce phenolic solvent components.

BRIEF SUMMARY

According to an embodiment of the disclosed subject matter, a process may include converting biomass into furfural. The process may include (a) providing a pentosan-containing biomass material and (b) subjecting the pentosan-containing biomass material to an acid catalyzed digestion process in a digestion vessel at a temperature greater than about 100° C. for a period of time sufficient to produce a digested product stream comprising C5-carbohydrates and solids comprising cellulose. Next, in step (c), the digested product stream may be separated into a liquid product stream and a solid product stream. The liquid product stream may comprise carbohydrate compounds, of which at least 50 wt % of the carbohydrate compounds are C5-carbohydrate compounds, based on the weight of carbohydrate compounds in the liquid product stream. The solid product stream may comprise solids including lignin and cellulose. In step (d), the solids product stream may be contacted with water and an organic solvent, thereby converting at least part of the lignin to a phenolic solvent, to produce a solvent product stream comprising the phenolic solvent and solids. Next, in step (e), the C5-carbohydrate in the liquid product stream may be subjected to a dehydration reaction in a reaction vessel at a temperature in the range of from about 100° C. to about 250° C. in the presence of an acid catalyst and a biphasic mixture comprising an aqueous phase and a water-immiscible organic phase for a period of time sufficient to produce furfural or a furan derivative. The water-immiscible organic phase may include at least a portion of the phenolic solvent produced in step (d). Next, from the reaction vessel a dehydration product stream may be retrieved comprising water, organic solvent and furfural. The dehydration product stream may be separated into an aqueous recycle stream and an organic product stream comprising furfural. The furfural may be recovered from the organic product stream by at least one separation process and the organic product stream from step (g) may be recycled back to the reaction vessel in step (e).

Implementations of the disclosed subject matter provide a process for the conversion of biomass to furfural and the preparation of lignin-based solvents used in the process for converting biomass to furfural and furfural derivatives. The disclosed subject matter allows for the preparation of lignin-based solvents used in the process for making furfural. This disclosed process results in a more efficient process by reducing the demand for purchased organic solvent to be provided to the process. Also, these phenolic solvents can efficiently extract furfural from the aqueous phase that may be present in the aqueous phase. Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Figure 1:
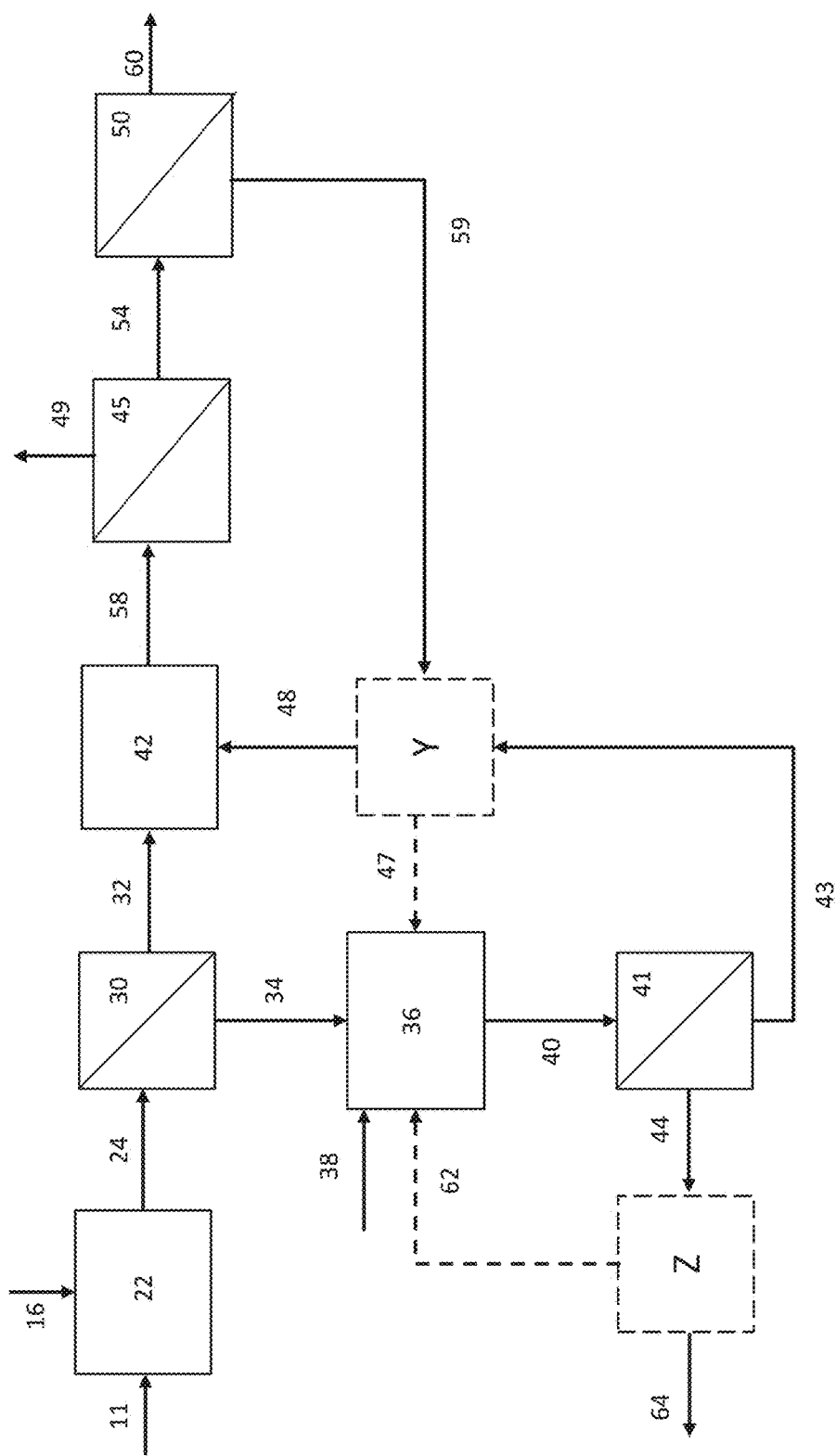
FIG. 1 shows an example schematic process diagram for producing furfural from biomass according to an implementation of the disclosed subject matter.

The presently disclosed subject matter provides an improved method for the production of furfural from biomass in a batch, continuous or semi-continuous manner, (optionally as a closed-loop process) as taught in WO2016025679, WO2016025678, WO2016025677, WO2016025674, and WO2016025673. In particular, the presently disclosed subject matter provides methods and processes for the production of valuable organic products from pentosan-comprising biomass materials using an efficient process having numerous advantages over prior production methods. In general, a process for producing furfural from biomass may include a digestion step followed by a subsequent dehydration step. The subsequent dehydration step may include use of an acid catalyst and biphasic mixture comprising an aqueous phase and a water-immiscible organic phase. The water-immiscible organic phase may include one or more organic solvents, and accordingly, the process may require a constant input volume of fresh organic solvent e.g. to compensate for solvent lost in the solvent recycle loop. The presently disclosed subject matter provides for the preparation of lignin-based solvents for use as an organic solvent in the water-immiscible organic phase. As a result, the process decreases the need for fresh organic solvent(s) during the process due to the ability to prepare a lignin-based solvent and provide such solvent to the dehydration step of the process, as disclosed herein. This offers the advantage of decreasing the input volume of organic solvents necessary to the reaction process and associated costs of feeding fresh organic solvent(s) into the process thereby increasing the efficiency of organic solvent usage throughout the process.

DEFINITIONS

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further in this connection, certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

The term "biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar, protein and oil such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks and corn stover, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. The term "biomass" includes virgin biomass and/or non-virgin biomass such as agricultural biomass (such as grains, e.g., corn, wheat and barley; sugarcane; cone stover, corn cobs and other inedible waste parts of food plants; grasses such as switchgrass), forestry biomass (such as wood and waste wood products), commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like. In some embodiments, the lignocellulosic biomass is selected from the group including, but not limited to, corn stover, straw, bagasse, miscanthus, sorghum residue, switch grass, bamboo, water hyacinth, hardwood, hardwood, softwood, wood chips, and wood pulp.

As used herein the term "pentosan" refers to a polysaccharide containing C5 carbohydrates monomers.

As used herein, the term "carbohydrate" is defined as a compound that consists only of carbon, hydrogen, and oxygen atoms, wherein the ratio of carbon atoms to hydrogen to oxygen atoms is 1:2:1 for monomeric carbohydrates. In general, oligomeric carbohydrates contain less water. Carbohydrate derivatives may also be considered, e.g., acetylated sugars found in hemicellulose in which —OH is replaced with —OOCCH3. Well known examples of carbohydrates include sugars and sugar-derived oligomers and sugar-derived polymers.

As used herein, the term "lignocellulosic" means, comprising cellulose, lignin and hemicellulose and/or pentosan.

As used herein, the term "hemicellulosic" refers to a material comprising C5 and C6 sugar polymers. Hemicellulose consists of short, highly branched chains of sugars. It contains five-carbon sugars (usually D-xylose and L-arabinose) and six-carbon sugars (D-galactose, D-glucose, and D-mannose) and uronic acid. The sugars are partially acetylated. Typically, the acetyl content is 10 to 15 wt %, based on the hemicellulose or 2 to 3 wt %, based on the biomass.

The relative content of C5 versus C6 sugars produced from hemicellulose depends on the source of the hemicellulose. When hydrolyzed, the hemicellulose from hardwoods releases products rich in xylose (a five-carbon sugar). The hemicellulose contained in softwoods, by contrast, yields more six-carbon sugars. The branched nature of hemicellulose renders it amorphous and relatively easy to hydrolyze to its constituent sugars compared to cellulose.

The term "furfural", or "2-furaldehyde", as used herein, refers to the organic compound having the molecular formula $C_5H_4O_2$ and the structure shown below.

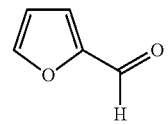

As used herein, the term "miscible" refers to a mixture of components that, when combined, form a single liquid phase (i.e., the mixture is "monophasic") under specified conditions (e.g., component concentrations, temperature).

As used herein, the term "immiscible" refers to a mixture of components that, when combined, form a two, or more, phases under specified conditions (e.g., component concentrations, temperature).

As used herein, the term "monophasic" refers to a reaction medium that includes only one liquid phase. Some examples are water, aqueous solutions, and solutions containing aqueous and organic solvents that are miscible with each other. The term "monophasic" can also be used to describe a method employing such a reaction medium.

As used herein, the term "biphasic" refers to a reaction medium that includes two separated liquid phases, for example, an aqueous or water-rich phase and an organic or organic solvent-rich phase. The term "biphasic" can also be used to describe a method employing such a reaction medium.

As used herein the term "water-miscible organic solvent" refers to an organic solvent that can form a monophasic solution with water at the temperature and concentration at which the reaction is carried out.

As used herein, the term "immiscible" refers to a mixture of components that, when combined, form a two, or more, phases under specified conditions (e.g., component concentrations, temperature).

Unless otherwise defined, all technical and scientific terms used herein have the same meaning as commonly understood by one of ordinary skill in the art to which this invention belongs. In case of conflict, the present specification, including definitions, will control.

The term "C5 carbohydrates" refers to any carbohydrate, without limitation, that has five (5) carbon atoms in its monomeric unit. The definition includes pentose sugars of any description and stereoisomerism (e.g., D/L aldopentoses and D/L ketopentoses). C5 carbohydrates can include (by way of example and not limitation) arabinose, lyxose, ribose, ribulose, xylose, and xylulose, in their monomeric, oligomeric and polymeric forms. Polymeric C5 carbohydrates can contain several C5 carbohydrate monomers and in some instances even contain some (lesser) amount of C6 carbohydrate monomers.

Biomass Processing

FIG. 1 shows an example process scheme according to an embodiment of the disclosed subject matter. As shown, the biomass material 11 can be used in a wet, dry or substantially dry form, and introduced directly into a digestion vessel 22 (also referred to herein as a digester), and may be pre-ground or not. For example, the biomass material used can be sized by grinding to a desired particle size prior to introduction to the digester 22. In a non-limiting example, the biomass can be ground to a particle size in the range of about 0.1 mm to about 10.0 mm, about 0.1 mm to about 5.0 mm, or about 0.1 mm to about 2.0 mm. In the instance that the biomass is ground and/or sized to a specific particle size, the particle size can be selected such that the digestion process occurs with the highest efficiency.

The biomass material 11, whether ground or not, can also be mixed with water to form a slurry of a desired consistency prior to introducing the biomass to the digester 22. For example, the slurry can be in the range of from about 5 wt % solids to about 100 wt % solids by weight, e.g., about 10 wt %, about 20 wt %, about 30 wt %, about 40 wt %, about 50 wt %, about 60 wt %, about 70 wt %, about 80 wt %, about 90 wt %, or about 100 wt % solids by weight.

In accordance with select aspects of the present invention, the biomass material 11 that is advanced to the digester 22 may further include or be mixed with an aqueous liquid (water) or liquids from other, downstream steps in the process. The biomass material 11 may optionally also be separated into a liquid phase and a solids phase using any suitable separation method, including centrifugation, decanting, filtration and flocculation, so as to concentrate or adjust the biomass in the initial steps of the process to optimize production.

Digestion

As shown in FIG. 1, in the next step of the production process, the biomass material 11 is introduced into a digester 22, using any suitable introducing/feeding methods, such as via a screw extruder, conveyor belt, piston or centrifugal pump, lock hopper or by way of a material addition pipe stream.

In the digestion step, the biomass is either admixed with an aqueous liquid (e.g., water) to a target solid-to-liquid (S:L) concentration, or if already in slurry form, adjusted to the appropriate concentration ratio. The solid to liquid weight ratio within the digester 22 preferably ranges from about 1:3 to 1:30, preferably about 1:3 to about 1:15, more preferably from about 1:6 to about 1:15, still more preferably from about 1:6 to about 1:10, even still more preferably from about 1:8 to about 1:10. The digestion process step is carried out at an elevated temperature, preferably above about 100° C., including in the range from about 100° C. to about 250° C., and from about 110° C. to about 160° C., for a period of time ranging from about 1 minutes to about 8 hrs, preferably from about 5 minutes to about 4 hrs.

The digestion step may also include the addition of one or more acids, or buffer solutions, to the digester 22 via acid stream 16, so as to adjust the pH of the digestion reaction and maintain it with a selected pH range. Preferably, the pH is less than about pH 5, more preferably less than about pH 3, and most preferably less than about pH 1. Preferably, a pH range is used in the range of from 0 to 5, more preferably of from 0 to 4, even more preferably of from 0 to 3, still more preferably of from 0 to 2. Any suitable digester equipment known in the art may be used.

In accordance with preferred aspects of the invention, the acid catalyst introduced into the digester is introduced by an acid stream 16 and is introduced in amounts and at a rate so as to optimize the digestion process. The acid catalyst may be an inorganic acid, a mineral acid such as HCl, $HNO_3$, $H_2SO_4$, $H_3PO_4$, $H_3BO_3$, and the like. Organic acids (e.g., acetic acid, formic acid, oxalic acid, levulinic acid, citric acid, etc.) may also be used. The acid catalyst may also be α-hydroxysulfonic acid which is produced from (a) a carbonyl compound or a precursor to a carbonyl compound with (b) sulfur dioxide or a precursor to sulfur dioxide and (c) water. The α-hydroxysulfonic acids have the general formula

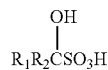

wherein R1 and R2 are individually hydrogen or hydrocarbyl with up to about 9 carbon atoms that may or may not contain oxygen can be used in the treatment of the instant invention. The alpha-hydroxysulfonic acid can be used as a mixture along with aforementioned acids, for example, as described in WO2016025673. The acid catalyst used in the digestion process may be any acid or combinations thereof as described herein. Enzymes may also optionally be added (not shown) during the digestion step to enhance or optimize the digestion process. In an embodiment, the α-hydroxysulfonic acid may be at least one of alpha-hydroxyethanesulfonic acid or alpha-hydroxymethanesulfonic acid.

In one particular example, some types of biomass that may be used as the starting material intrinsically contain acids or will form acids upon being subjected to the digestion, examples of such acids intrinsically contained or formed include, but are not limited to, formic acid or acetic acid. When using such types of biomass, the need to add acid may be reduced or even eliminated as the in-situ generated acid will provide the necessary acidic pH.

The amount of acid to be added, or the amount present within the digestion slurry, is preferably adjusted to be in the range from about 0.1 wt % to about 10 wt % acid.

Separation

With continued reference to FIG. 1, once the digestion process is complete, the digestion process stream 24 is transferred to a first separator section 30, preferably a solid-liquid separator or other phase separator, where a solid product stream 34 comprising residual product is separated from the aqueous C5 sugar-containing feed stream 32 that contains primarily C5-carbohydrate products, such as xylan, as a majority of the liquid product stream. The residual product may typically contain primarily cellulose or derivatives thereof and lignin. The aqueous C5 sugar-containing feed stream 32 is then fed into a reaction vessel 42 for the dehydration step. Optionally, part of stream 32 may be recycled to digester 22. This has the advantage that the C5 sugar content may be increased in stream 32.

Preparation of Lignin-Based Solvent

Returning to FIG. 1, the solid product stream 34 may comprise solids including lignin and cellulose. In step (d), this solid product stream 34 may be fed to a reactor 36 in which the solids product stream may be contacted with an organic solvent and optionally water via stream 38. As a result, at least part of the lignin may be converted to a phenolic solvent to produce a solvent product stream 40 comprising the phenolic solvent and solids. Examples of organic solvent include methanol, ethanol, propanol, 1 or 2 butanol, acetone, tetrahydrofuran, methyltetrahydrofuran, acetic acid, formic acid, lactic acid, levulinic acid, C3-C6 diols, C3-C6 glycols, gVL (i.e., gammavalerolactone), furfuryl alcohol, and tetrahydrofurfuryl alcohol, aromatic solvents (e.g., toluene, xylene, napthalenes, methylnaphthalenes, etc.), phenolic solvents (e.g., Sec-butylphenol, eugenol, guaicol, nonyl phenol, etc.) and mixtures thereof.

The solvent product stream 40 may be fed to a separator 41, preferably a solid-liquid separator or other phase separator, where solids may be separated from the solvent product stream. Stream 43 may be the resulting solvent product stream from which solids have been removed. Next, the solvent product stream 43 may be fed directly to the dehydration vessel 42 for use in the dehydration step (e). For example, the organic solvent used in step (e) may be the same as organic solvent in step (d).

A solid stream 44 may include the separated solids such as cellulose and remaining lignin. In an embodiment, solid stream 44 may be optionally further processed as depicted by optional Unit Z shown in FIG. 1. For example, solid stream 44 may be further processed to remove any organic solvent present in the solid stream. Unit Z may be a dryer/evaporator to remove the remaining organic solvent via stream 62 which may be recycled back to step (d). A separated product stream 64 may include the separated solids, free from solvent. For example, solids in the solids product stream may be converted into alcohol, glycol, polyols, acid, diacid, hydroxyacid, ketoacid (levulinic acid), furans (HMF), power, energy, or a fuel gas.

FIG. 1 shows optional Unit Y for further processing of the solvent product stream 43, although solvent product stream 43 may be fed directly to the dehydration vessel 42 for use in the dehydration step (e). As shown by Unit Y in FIG. 1, optional additional steps may be performed prior to step (e). In an embodiment, Unit Y may be a separator for separating the phenolic solvent from the solvent product stream 43 (as described in further below).

According to an embodiment, Unit Y may be a separator and the solvent product stream 43 may be fed to the separator, preferably a liquid-liquid separator, a vapor-liquid separator or other phase separator, in which at least part of the phenolic solvent may be separated from the solvent product stream 43. A liquid stream 47 may include water and/or the organic solvent, and in an embodiment, water and the organic solvent may be removed from the separator via a separate stream for each. Optionally, liquid stream 47 including water and/or the organic solvent may be recycled back to and fed to the reactor 36. Stream 48 may include the separated phenolic solvent and may be fed to the dehydration vessel 42 for use in the dehydration (step (e)), as described in further detail below.

In an embodiment of the disclosed subject matter, the separated phenolic solvent in stream 48 may be subjected to further processing prior to being fed to the dehydration vessel 42 for use in the dehydration step (e). For example, although not shown, at least part of the separated phenolic solvent from stream 48 may be further subjected to a catalytic conversion step thereby converting at least part of the separated phenolic solvent to a monomeric phenolic solvent prior to step (e). Examples of the catalytic conversion step include hydrogenolysis, pyrolysis, base hydrolysis, and a hydrodeoxygenation reaction. As a result of this catalytic conversion step, the produced monomeric phenolic solvent may be fed to the dehydration vessel 42 for use in the dehydration step (e) in the water-immiscible organic phase.

In an embodiment, Unit Y may be a unit for upgrading the solvent product stream via a conversion step or depolymerization step. As a result of this upgrading step, the produced upgraded phenolic solvent may be fed to the dehydration vessel 42 for use in the dehydration step (e) in the water-immiscible organic phase. Optionally, following this upgrading in Unit Y, the upgraded phenolic solvent may be further separated and may be fed to the dehydration vessel 42 for use in the dehydration step (e) in the water-immiscible organic phase. further comprising, prior to step (e), upgrading the solvent product stream comprising the phenolic solvent in step (d), and wherein the phenolic solvent in step (e) is at least a portion of the upgraded phenolic solvent.

Biphasic System

In the process according to the invention, an aqueous C5 sugar-containing feed stream 32, preferably prepared as described herein above, is provided as a feed to the process to produce furfural or furfural derivatives (step (e)). In step (e), the aqueous C5-sugar feed stream is comprised in an aqueous phase and contacted with a water-immiscible organic phase comprising an organic solvent and at least a portion of the phenolic solvent (e.g., stream 43) from step (d) described above. The aqueous phase may comprise, consist or essentially consist of the aqueous C5 sugar-containing feed stream. Preferably, aqueous phase and the organic phase when contacted form a biphasic system. Preferably, the aqueous phase and the organic phase are immiscible. However, it is not necessary to have two phases at reaction temperature, although it may be helpful to have two phases less than 50° C. to allow for liquid-liquid split and furfural extraction. The preferred water-immiscible organic phase for use in the presently disclosed subject matter comprises at least a portion of the phenolic solvent in stream 48 (or stream 43 if optional Unit Y is excluded) prepared in step (d). According to an embodiment, the water-immiscible organic phase may include the phenolic solvent prepared in step (d) as well as one or more organic solvents that are immiscible with the aqueous phase containing the C5-sugars. Where the organic phase comprises two or more organic solvents, the individual organic solvents may be to some extent miscible with water, as long as the mixture of the organic solvents is essentially immiscible, i.e. form a biphasic system, with the aqueous phase at 25 to 50° C. Preferably such water-immiscible organic solvents have a maximum water solubility of less than about 30 wt %, preferably less than about 10 wt %, and most preferably less than about 2 wt % at ambient (room) temperature.

However, the organic phase may also include other organic solvents such as 1-butanol, sec-butyl phenol (SBP), methylisobutyl ketone (MIBK), and dichloromethane (DCM). Other organic phases, especially other alcohols, ketones, and halogenated alkanes, may also be utilized. Thus, for example, organic solvents such as straight or branched alcohols (e.g. pentanol, tertbutyl alcohol, etc.), cyclic alcohols (e.g., cyclohexanol), straight or branched alkanones (e.g. butanone, pentanone, hexanone, heptanone, diisobutylketone, 3-methyl-2-butanone, 5-methyl-3-heptanone, etc.), and cycloalkanones (e.g., cyclobutanone, cyclopentanone, cyclohexanone, etc.) may be used in the present invention. Nitriles (such as benzonitrile), aliphatic and cycloaliphatic ethers (e.g., dichloroethylether, dimethyl ether, diethyl ether, dibutyl ether), saturated and unsaturated aliphatic or aromatic hydrocarbons (decane, toluene, benzene, cymene, 1-methyl naphthalene), phenolic solvents (sec-butyl phenol, eugenol, methoxy methylphenol, nonyl phenol, cresol, guaiacol, anisol), and nitroalkanes (e.g., nitromethane, nitropropane, etc.) may also be used. Likewise, halogenated derivatives of the above-noted compounds, as well as other halogenated alkanes may also be used as the organic phase (e.g., chloromethane, trichloromethane, trichloroethane, and the like).

Preferably, the organic solvent or the combination of organic solvents can extract 80 mol % or more of the furfural produced from the aqueous phase, while at the same time dissolve less than 1 wt %, more preferably less than 0.1 wt %, more preferably less than 0.01 wt % of water, based on the organic solvent.

The organic phase may be contacted with the aqueous phase in any volume suitable to form a biphasic system with the aqueous phase. Preferably, the weight of the organic phase is in the range of from 5 to 95% by weight, based on the combined weight of the aqueous phase and organic phase.

Dehydration

In the dehydration reaction vessel 42, the aqueous phase and water-immiscible organic phase are contacted at a temperature above about 100° C., preferably in the range of from about 100 to 300° C. to effectuate a dehydration reaction, wherein C5 sugars are dehydrated to furfural. Preferably, the aqueous phase and water-immiscible organic phase are contacted at a temperature in the range of from at least about 100° C., about 110° C., about 140° C. and to less than about 180° C., about 200° C., and about 250° C. The dehydration reaction may be carried out for a period of time ranging of from about 1 second to about 24 hrs, preferably for a period of time ranging of from about 1 minute to about 12 hrs, more preferably from about 3 minutes to about 6 hours, still more preferably 10 minutes to 4 hrs., even still more preferably 15 minutes to 2 hours or for times within these ranges. One or more acid catalysts as described herein may be added in order to catalyze the reaction process, for example, mineral acids such as $H_2SO_4$, HCl, $H_3PO_4$ and the like.

The solid acid catalyst used in the dehydration step can be a heterogeneous solid acid catalyst as long as it can catalyze the dehydration of C5 carbohydrates to furfural and/or its derivatives. Preferred heterogeneous solid acid catalyst, may include acidic ion exchange resins, for example, such as sulfonated resins (e.g., polystyrene sulfonate), acidic zeolites, for example, such as HZSM-5 HY, HUY and HUSY zeolites (e.g., with 0.5 to 0.74 nm pore diameters) β-zeolite (e.g. Si/Al=12), H-beta (e.g., Si/Al=19), layered clays such as amorphous silica alumina, gamma alumina, mesoporous silicate and aluminosilicates such as MCM-41, aluminum incorporated mesoporous silica, for example, such as Al-MCM-41, and AL-SBA-15, sulfonic acid functionalized metal oxides such as sulfated tin oxides, and microporous silicoaluminophosphates (SAPO), perfluorinated ion-exchange materials such as Nafion® SAC-13 and Nafion-117, sulfonated grapheme oxide, and heteropolyacids. Commercial examples of acidic ion exchange resin catalysts includes, for example, DOWEX™ HCR-S, DOWEX HCR-W2, DOWEX M-31, DOWEX G-26, DOWEX DR 2013, Amberlyst™ 70 (available from Dow Chemical Co.) and Amberlyst® 15 (wet) ion-exchange resin, AMBERJET™ 1200 (H) ion exchange resin, Amberlite® IR-118 (H), Amberlite® IR-120 (plus), Amberlite 15, Amberlite® XN-1010, and Nafion® Resins (available from Sigma-aldrich Co.) Commercial example of amorphous silica alumina catalyst include, for example X-600 catalyst (available from Criterion Catalysts & Technologies L.P.).

The concentration of the C5 sugars in the dehydration reactor 42 can vary depending upon the product to be obtained. However, in accordance with aspects of the present invention, it has been found that the reaction is optimized for obtaining furfural or other furan derivatives when the concentration of C5 sugars in the aqueous phase is in the range of from about 0.1 to 20 wt %, more preferably of from about 0.2 to 10 wt %, based on the weight of the aqueous phase.

Due to the preference of the formed furfural to reside in the organic phase rather than in the aqueous phase at least part of the formed furfural, and preferably more than 50 mol %, still more preferably more than 75 mol %, even still more preferably more than 80 mol % of the formed furfural will dissolve in the organic phase. The thus formed furfural-containing organic phase is subsequently separated from the aqueous phase.

Product Recovery

Referring back to FIG. 1, aqueous C5 sugar-containing feed stream 32 is provided to dehydration reactor 42 as an aqueous phase to a dehydration process step together with a portion of the phenolic solvent 48 (or stream 43 if optional Unit Y is excluded) as the organic phase. After the dehydration step, step (f) may include retrieving from the reaction vessel a dehydration product stream 58 comprising water, organic solvent and furfural, and separating the dehydration product stream into an aqueous recycle stream and an organic product stream comprising furfural. In an embodiment, step (g) may include recovering the furfural from the organic product stream by at least one separation process. The furfural in the furfural-containing organic phase may be retrieved from the process as product and may be used to prepare one or more furfural derivatives. According to an embodiment, the furfural concentration may be about 0.1 to 15 wt %. As shown in FIG. 1, the dehydration product 58, i.e. the aqueous phase and furfural-comprising organic phase are provided to second separation section 45, to be separated into a C5 sugar-depleted aqueous stream 49 and a stream comprising the furfural-containing organic phase 54. Further, according to an embodiment, in step (h), the organic product stream from step (g) may be recycled back to the reaction vessel in step (e).

As shown in FIG. 1, stream 54 is provided to a third separation section 50, preferably including one or more distillation steps, wherein a furfural-containing product 60, optionally containing other furan derivatives is isolated, while in step (h) a residual organic stream 59 is recycled back to the dehydration step 42. Optionally, stream 58 may be treated to remove the solid byproducts, e.g. via filtration, before entering a separation section. The additional separation may preferably be a liquid/liquid extraction step.

The aqueous stream 49 may be recycled and be either fed directly back (not shown) into the process to the digester 22 in step (b), or, depending upon the salt content of the aqueous stream, can undergo a further separation (not shown) to remove unwanted or excessive amounts of salts and/or solids, the remaining aqueous stream being reintroduced to the digester 22 (not shown).

Cellulosic Residue

The residual product 44 may be further processed to prepare further valuable products (not shown). Typically, the residual product 44 contains C6 sugars or its derivative, oligomer and polymers. The residual product can be sent to a hydrolysis step, followed by a fermentation step to yield one or more commercially important alcohol or acid products. The C6 containing residue may also be processed using chemo-catalysis to produce various valuable intermediates such as HMF, levulinic acid, C6 sugar alcohols, short alcohols, diols, polyols, ketones and aldehydes and the derivative thereof in pure or mixed form. Residual product 44 may also be burned in a boiler to produce steam and power.

Other and further embodiments utilizing one or more aspects of the inventions described above can be devised without departing from the spirit of Applicant's invention. For example, two or more catalysts can be used, separately or in combination, in one or more reactors, in one or more stages. Further, the various methods and embodiments of the methods of manufacture and assembly of the system, as well as location specifications, can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

EXAMPLES

General Methods and Materials:

Digestion

All the digestion experiments were carried out in a 2 L parr batch reactor. Biomass (eg. bagasse) is weighed and placed in the reactor. The composition of the biomass (bagasse) charged is given in Table 1. After the reaction is complete the aqueous liquor is separated from the treated product mixture using a filtration apparatus using house vacuum system. The content of the aqueous liquor is analyzed for carbohydrate composition. The residual biomass is used for solids analysis. Compositional analysis of the residual biomass is carried out to determine the carbohydrate and lignin content.

Phenolic Solvent Production Step

All the experiments were performed in a 500 ml Zipperclave batch reactor (Autoclave Engineers). The residual biomass (eg. bagasse) prepared from above-mentioned digestion step was weighed and placed in the reactor. The reactor was then charged with a mixture of solvent and water as indicated in the Example 4-8. After the reaction was complete, the reaction liquid is separated from the treated product mixture using a filtration apparatus using house vacuum system. The residual biomass is dried and weighed accurately to know how much lignin is extracted based on the solid feed to this processing step. The liquid sample is then taken to a rotary evaporator to remove the solvent components leaving behind a precipitate which constitutes the phenolic solvent.

Biphasic Dehydration

The biphasic acid dehydration of C5 carbohydrates (primarily xylose) containing aqueous liquid stream was carried out in a 500 ml zipperclave reactor (Autoclave Engineers, Inc.) and/or a 300 ml Parr autoclave. In a typical run, acidified C5 carbohydrate feed aqueous stream was added to the reactor along with an immiscible organic solvent with a certain Aqueous: Organic ratio on weight basis. The organic solvent used in this case can be derived from the phenolic solvent prepared by the above mentioned production step as illustrated in Example 9. The reactor is then heated to the reaction temperature and held at that temperature for the residence time indicated in the Example 9. After the reaction is complete the reaction mixture were weighed and transferred into a separatory funnel to allow for two liquid phases to separate. After separation, each layer was weighed and analyzed for its content. Aqueous layer was analyzed using HPLC and the Organic layer was analyzed using GC as described below.

Analytical Methods

Solids compositional analysis of the feedstock the digested biomass samples were conducted using standard TAPPI (T-222, T-211, T-249) methods.

The aqueous layers from digestion and dehydration runs were analyzed and quantified for various components such as glucose, xylose, arabinose, mannose, formic acid, acetic acid, levulinic acid, furfural using high-performance liquid chromatography (HPLC) system (Shimadzu) equipped with a refractive index detector (Shimadzu) on a BIO-RAD 87H Column. Prior to injection, the samples were filtered through 0.45 μm HV filters (Millipore, Bedford, Mass., USA), and a volume of 10 μL was injected. The mobile phase for the column was 5 mM H2SO4 in Milli-Q water at a flow rate of 0.6 mL/min.

In a typical biphasic dehydration run the furfural concentration in the organic phase or layer was measured using GC. Agilent 6890 GC with a DB-1301 capillary column installed in its split/splitless inlet was used with the FID. The column parameters were 30 m length, 0.25 mm ID, and 1.0 μm film thickness. Method parameters were as follows:

Oven Temp Program—40 C Hold 3 min, Ramp 10 C/min to 280 C Hold 3 min

Inlet Temp 250 C, Injection Volume 1.0 μl, Split ratio 100:1, Constant Pressure 20 psi Helium Carrier gas Detector Temp 325 C, H2 flow 35 ml/min, Air 400 ml/min, and Helium Makeup 25 ml/min Calculations Solids dissolved was calculated as weight percentage ratio of oven dried digested biomass material to the total amount of feed (on dry basis).

Xylan removal accounts for how much xylan is removed during digestion based on component analysis of the pretreated solids.

$$\text{Xylose Conversion} = \{[\text{mole of Xylose}]_{feed} - [\text{mole of Xylose}]_{AL}\}/[\text{mole of Xylose}]_{feed}$$

$$\text{Furfural Selectivity} = \{[\text{moles of FUR}]_{AL} + [\text{moles of FUR}]_{OL}\}/\{[\text{mole of Xylose}]_{feed} - [\text{mole of Xylose}]_{AL}\}$$

Biomass Composition

TABLE 1

| Biomass (Bagasse) composition used BAGASSE COMPOSITION (wt % on dry basis) | | |
|---|---|---|
| CELLULOSE | 40 | |
| HEMICELLULOSE | 28.5 | |
| Glucoronic Acid | | 0.7 |
| Xylose | | 22.8 |
| Arabinose | | 2.2 |
| Acetic Acid | | 3.9 |
| TOTAL LIGNIN | 18 | |
| Acid Insoluble Lignin | | 16.75 |
| Acid Soluble Lignin | | 1.25 |
| TOTAL ASH | 3.5 | |
| EXTRATIVES (Ethanol) | 9.75 | |
| TOTAL | 99.75 | |

Examples 1-3: Biomass Xylan Removal Using Acid Mixtures

For each run, biomass (bagasse) was charged into a batch reaction vessel described above at a biomass to liquid (water) ratio of 1:8. The reactions were performed for a certain period of effective residence time, given acid concentration using 5 wt % alpha-hydroxyethane sulfonic acid (HESA) and 1 wt % $H_2SO_4$ acid mixture and temperature as indicated in the Table 2. The reaction mixture was then filtered and the filtrate collected and analyzed via HPLC for xylan recovery (including xylose and furfural formed). The solid was washed with water, filtered and dried to measure amount of dissolved solids. The wet solids were washed with water, and the wet cake dried in a drying oven equipped with a vacuum trap (to collect solvent and/or water), and analyzed for content. As seen in Table 2 about 75-85% of the xylan is removed via digestion step with about 30-40% solids dissolved. The leftover pretreated solids were subsequently used for production of phenolic solvent.

TABLE 2

Digestion of bagasse for xylan removal and phenolic acid production

| Run # | T [C.] | Time (mins) | Acid (H2SO4) [wt %] | RAPT Acid HESA [wt %] | Solids Dissolved (%) | Xylan Removed (%) |
|---|---|---|---|---|---|---|
| 1 | 130 | 15 | 1 | 5 | 36 | 79 |
| 2 | 130 | 20 | 1 | 5 | 38 | 82 |
| 3 | 130 | 30 | 1 | 5 | 40 | 85 |

Examples 4-8: Production of Phenolic Solvent Using Digested Solids

All the experiments were performed in a 500 ml Zipper-clave batch reactor (Autoclave Engineers). About 15 gm of dried pretreated biomass (eg. bagasse) prepared from above-mentioned digestion step was weighed and placed in a batch reactor. The reactor was then charged with 150 gm of mixture of solvent and water as indicated in the Example 4-8. The extraction reaction was conducted at temperature and time as indicated in Table 3. The reaction liquid is separated from the treated product mixture using a filtration apparatus using house vacuum system. The residual biomass is then dried and weighed accurately to know how much lignin is extracted based on the solid feed to this processing step. The liquid sample is then taken to a rotary evaporator to remove the solvent components leaving behind a precipitate which constitutes the phenolic solvent. In the case of an aqueous/solvent miscible mixture, one can only remove the solvent, if light boiling as compared to water, and the phenolic solvent precipitates out from water. As seen in Table 3, about 10-15% of the phenolic solvent components are formed based on mass loss on the solids fed to the reactor.

TABLE 3

Results and conditions for phenolic solvent production step

| Run # | Solid from Run # | Solvent | Temp [C.] | Time [mins] | Amount of phenolic solvent formed based on solids removed from pretreated solids (g phenolic solvent/ 100 g solids feed) | Amount of phenolic solvent isolated after water/solvent removal (g phenolic solvent/ 100 g solid feed) |
|---|---|---|---|---|---|---|
| 4 | 1 | Water:Ethanol 50:50 (w/w) | 120 | 90 | 12.80 | 9.13 |
| 5 | 1 | Water:Ethanol 50:50 (w/w) | 90 | 90 | 10.13 | 5.80 |
| 6 | 2 | Water:acetone 50:50 (w/w) | 90 | 90 | 10.13 | 5.27 |
| 7 | 3 | Water:Toluene 50:50 (w/w) | 90 | 90 | 10.13 | 3.53 |
| 8 | 3 | Water:Toluene 50:50 (w/w) | 120 | 90 | 12.20 | 3.87 |

Example 9: Solvent Screening for Furfural Production Using Phenolic Solvent

Figure 2:
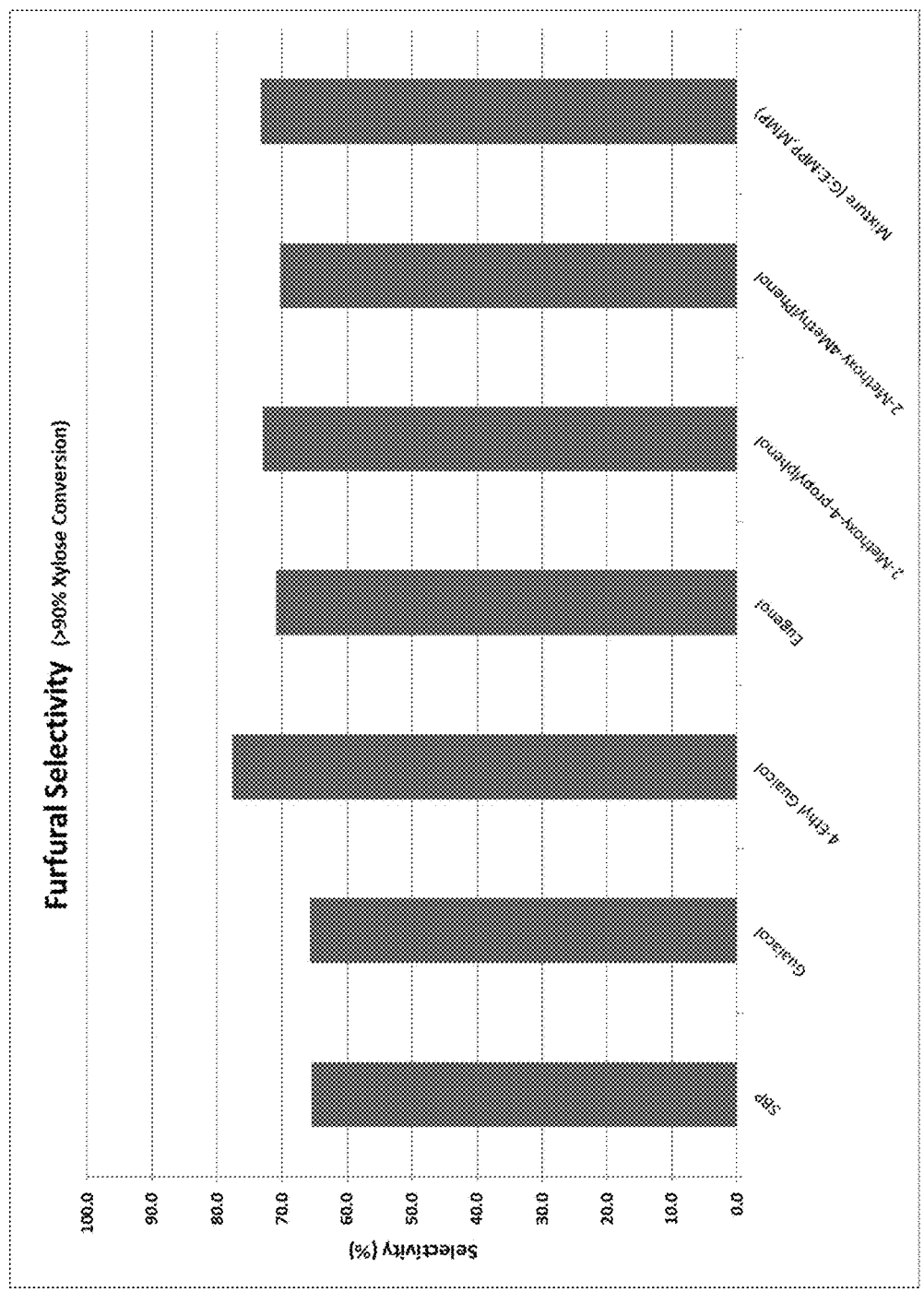
FIG. 2 shows furfural selectivity from xylose for various phenolic solvent components in a biphasic acid dehydration reaction system according to an implementation of the disclosed subject matter.

Various different phenolic solvents which can be derived from solids isolated from the above steps were screened for xylose selectivity towards furfural production in a biphasic dehydration system. In a typical run, 100 g of 5 wt % xylose solution (which can be assumed to be produced via various digestion runs) is prepared with 1 wt % $H_2SO_4$ acid concentration. Equal amount (100 g) of immiscible organic solvent is added to the reactor to create a biphasic reaction medium. The reactor was then heated to 170° C. and the temperature was held for a total time of 1 h from heating. In all cases conversion of xylose was more than 90% with the selectivity towards furfural as indicated in FIG. 2. FIG. 2 shows furfural selectivity from xylose for various phenolic solvent components in a biphasic acid dehydration reaction system. As can be seen from FIG. 2, the results show that various different types of lignin-derived phenolic solvents prepared from lignin extraction (phenolic solvent production) step can be used for furfural production. These solvent components or mixtures of these components can be derived via further processing of solids from lignin extraction steps indicated in the presently disclosed subject matter.

Example 10: Digestion Using α-Hydroxyethane Sulfonic Acid (HESA) Acid for Generation of Stream 1

Into a 1 gallon C276 Parr reactor fitted with in situ IR optics was added approximately 350 grams of compositionally characterized corn stover [dry basis: xylan 24% wt.; glucan 33% wt., 16% w moisture] chopped to nominal 0.5 cm particles. To this was added approximately 2600 grams of 5% wt. α-hydroxyethane sulfonic acid (HESA) prepared by the dilution of a 40% wt. stock solution of the acid, acid recycled from vaporization of components at the end of a reaction cycle, excessive pressate liquid from the bottoms after pressing the un-dissolved to about 20-22% w. Run targeted about 11% w fresh dry corn stover to begin a run. Target concentration of acid was confirmed by proton NMR of the starting mixture integrating over the peaks for water and the acid. The reactor top with a 4 blade down pitch impeller was placed on top of the reaction vessel and the reactor sealed. The pressure integrity of the reactor system and air atmosphere replacement was accomplished by pressurization with nitrogen to 100 psig where the sealed reactor was held for 15 minutes without loss of pressure followed by venting to atmospheric pressure. IR acquisition was initiated and the reaction mixture stirred at 500 rpm. The reactor was then heated to 120° C. and held at target temperature for 60 minutes. During this period of time the in situ IR reveals the presence of HESA, $SO_2$, and acetaldehyde in an equilibrium mixture. An increase in sugars is evident in the IR spectra, with an increase in the band height typical of xylose and glucose being apparent. At the end of the reaction period the acid reversal was accomplished via opening the gas cap of the reactor to an overhead condensation system for recovery of the acid and simultaneously adjusting the reactor temperature set point to 100° C. Vaporization from the reactor quickly cools the reactor contents to the 100° C. set point. The overhead condensation system was comprised of a 1 liter jacketed flask fitted with a fiber optic based in situ IR probe, a dry ice acetone condenser on the outlet and the gas inlet arriving through an 18" long steel condenser made from a core of ¼" diameter C-276 tubing fitted inside of ½" stainless steel tubing with appropriate connections to achieve a shell-in-tube condenser draining downward into the recovery flask. The recovery flask was charged with approximately 400 grams of DI water and the condenser and jacketed flask cooled with a circulating fluid held at 1° C. The progress of the acid reversion was monitored via the use of in situ IR in both the Parr reactor and the overhead condensation flask. During the reversal the first component to leave the Parr reactor was $SO_2$ followed quickly by a decrease in the bands for HESA. Correspondingly the bands for $SO_2$ rise in the recovery flask and then quickly fall as HESA was formed from the combination of vaporized acetaldehyde with this component. The reversal was continued until the in situ IR of the Parr reactor showed no remaining traces of the α-hydroxyethane sulfonic acid. The IR of the overheads revealed that the concentration of the HESA at this point had reached a maximum and then started to decrease due to dilution with condensed water, free of α-hydroxyethane sulfonic acid components, building in the recovery flask.

The reaction mixture was then cooled to room temperature, opened and the contents filtered through a Buchner funnel with medium filter paper using a vacuum aspirator to draw the liquid through the funnel. The wet solids are transferred from the Buchner funnel and placed in a filter press where an additional portion of liquid is pressed from the solids to create a high consistency biomass (about 22% w un-dissolved solids) mixture. The dry weight of solid is determined by washing a portion of the solids with water and then oven drying to a constant weight, a small portion of the combined liquid filtrate and pressate is removed for analysis by HPLC and NMR; the remainder is reserved for the next cycle with fresh biomass. A recycle experiment is accomplished by combining the primary filtrate and the pressate liquids with a sufficient quantity of HESA, either recycled from the overheads of the previous run or fresh acid from a 40% wt. stock solution, and water to yield 2600 grams of a 5% wt. acid solution which are returned to a 1 gallon C276 Parr reactor where it is mixed with another 350 gram portion of fresh biomass. The pretreatment cycle, venting and recovery, and filtration were repeated five times in addition to the initial starting run to produce the sample used in further experimentation. The HPLC analysis of the pressate is given below in Stream 1 (Table 4).

Example 11: Digestion Using α-Hydroxyethane Sulfonic Acid (HESA) Acid for Generation of Stream 2 and 3

Into a 7 gallon 316 stainless steel batch circulating digester approximately 1820 grams (29.14% w moisture) of compositionally characterized corn stover [dry basis: xylan 17.7% wt.; glucan 33% wt.] chopped to nominal 2 inch particles. A target fresh dry solids to liquids ratio being 9:1 being targeted for each run. The material was placed in a basket and is fixed during the run while liquid is circulated. The solids are removed at the end of the run after a free liquid drain and pressed to remove additional liquid. 1820 g of fresh stover (1290.5 g dry), 1452 g of 40% w of α-hydroxyethane sulfonic acid (HESA) stock solution, 2984 g make-up water, and 7549 g of recycle pressate (make-up water on run 1). The reactor was brought to 120° C. in about 10 minutes and held for 1 hour. The reactor was then vented to remove the bulk of the acid into a caustic scrubber. The acid was not recycled for this study and was made up from the stock solution for each run. Two streams (Stream 2 and 3) generated by this procedure with different xylose concentration were produced and analyzed as shown in Table 4.

TABLE 4

Composition of three streams produced using pressure reversible acid digestion of biomass

|  | Stream 1 | Stream 2 | Stream 3 |
| --- | --- | --- | --- |
| Cellobiose % | n/d | n/d | n/d |
| Sucrose % | n/d | n/d | n/d |
| Glucose % | 1.366 | 0.511 | 1.105 |
| Xylose % | 9.210 | 2.925 | 5.800 |
| Fructose % | n/d | 0.476 | 1.013 |
| Arabinose % | 1.371 | 0.037 | 0.070 |
| Formic % | 0.130 | 0.383 | 0.670 |
| Acetic % | 1.174 | 0.008 | 0.016 |
| HMF % | 0.014 | 0.053 | 0.093 |
| Furfural % | 0.149 | 0.003 | 0.003 |

Figure 3:
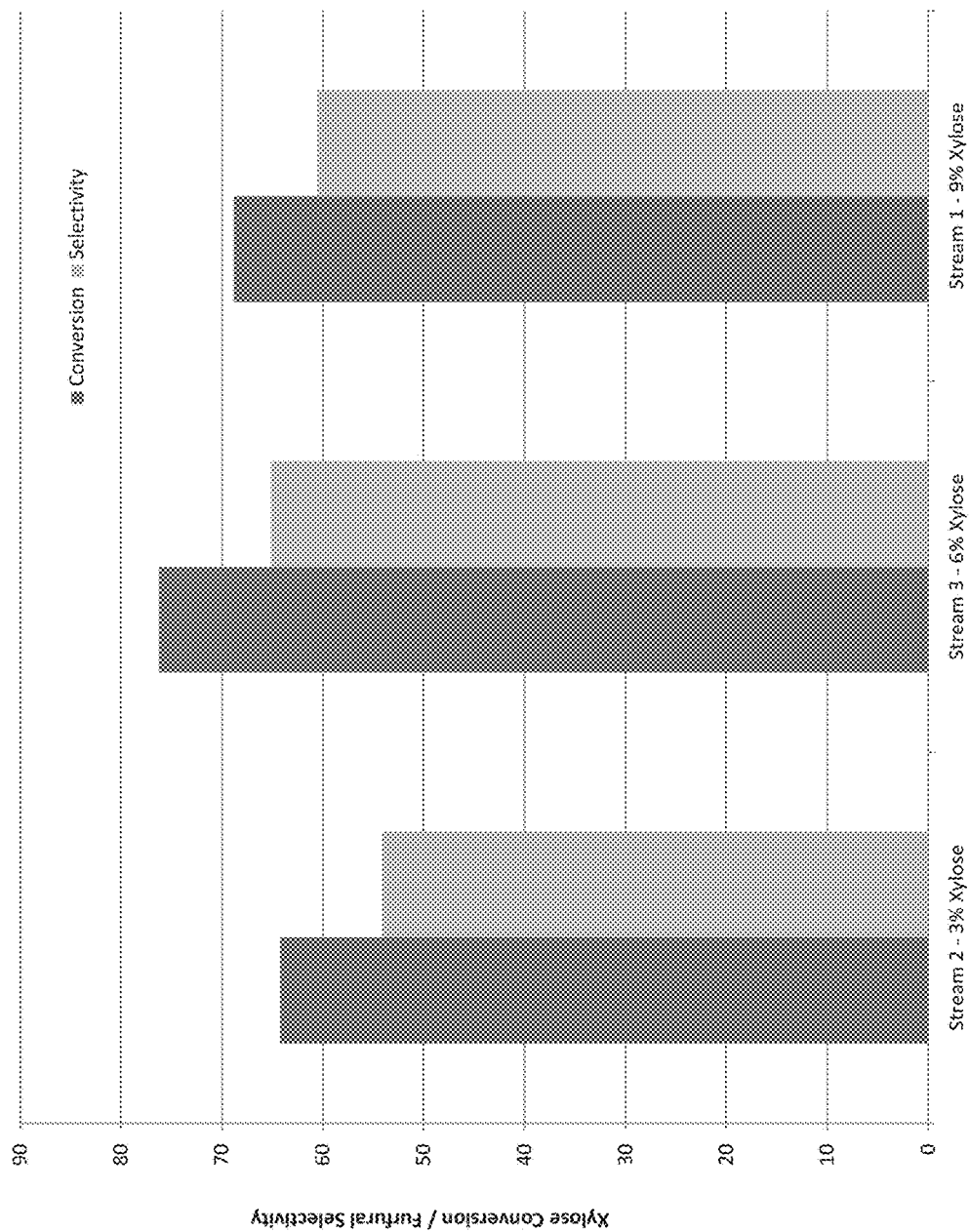
FIG. 3 shows the xylose conversion and furfural selectivity of a pressure reversible acid derived stream according to an implementation of the disclosed subject matter.

Example 12: Two-Phase Acid Dehydration of the Digested C5 Carbohydrate Containing Stream Using Phenolic Solvent For acid dehydration runs, three streams containing various xylose concentrations (as indicated in Table 4) were obtained using pressure reversible acid digestion step. Subsequently, acid dehydration runs were conducted by charging 100 g of aqueous xylose stream with added $H_2SO_4$ acid up to 1 wt % along with equal amount of extracting phenolic solvent such as sec-butyl phenol (SBP). The reactor was then heated to 170° C. and the temperature was held for a total time of 1 h from heating. After the reaction is complete the reactor is cooled to room temperature and the two liquid phases are separated. The aqueous layer was analyzed using HPLC and organic layer using GC for its content. The amount of xylose conversion and selectivity towards furfural is indicated in FIG. 3. FIG. 3 shows xylose conversion of pressure reversible acid derived stream to produce furfural. In all streams, furfural selectivity higher than 50% were observed with varying concentration of xylose in the feed.

That which is claimed is:

1. A process for converting biomass into furfural, the process comprising the steps of:
   (a) providing a pentosan-containing biomass material;
   (b) subjecting the pentosan-containing biomass material to an acid catalyzed digestion process in a digestion vessel at a temperature greater than about 100° C. for a period of time sufficient to produce a digested product stream comprising C5-carbohydrates and solids comprising cellulose;
   (c) separating the digested product stream into a liquid product stream and a solid product stream wherein:
      (i) the liquid product stream comprises carbohydrate compounds, of which at least 50 wt % of the carbohydrate compounds are C5-carbohydrate compounds, based on the weight of carbohydrate compounds in the liquid product stream,
      (ii) the solid product stream comprises solids comprising lignin and cellulose;
   (d) contacting the solid product stream with an organic solvent, thereby converting at least part of the lignin to a phenolic solvent, to produce solids and a solvent product stream comprising the phenolic solvent;
   (e) subjecting the C5-carbohydrate in the liquid product stream to a dehydration reaction in a reaction vessel at a temperature in the range of from about 100° C. to about 250° C. in the presence of an acid catalyst and a biphasic mixture comprising an aqueous phase and a water-immiscible organic phase, which comprises at least a portion of the phenolic solvent produced in step (d), for a period of time sufficient to produce furfural or a furan derivative;
   (f) retrieving from the reaction vessel a dehydration product stream comprising water, organic solvent and furfural, and separating the dehydration product stream into an aqueous recycle stream and an organic product stream comprising furfural;
   (g) recovering the furfural from the organic product stream by at least one separation process; and
   (h) recycling the organic product stream from step (g) back to the reaction vessel in step (e).

2. The process of claim 1, further comprising, prior to step (e), separating at least part of the phenolic solvent from the solvent product stream produced in step (d), and wherein the phenolic solvent in step (e) is at least a portion of the separated phenolic solvent.

3. The process of claim 1, further comprising: subjecting at least part of separated the phenolic solvent from step (d) to a catalytic conversion step thereby converting at least part of the separated phenolic solvent to a monomeric phenolic solvent prior to feeding to step (e), and wherein the water-immiscible organic phase in step (e) comprises the monomeric phenolic solvent.

4. The process of claim 3, wherein the catalytic conversion step is selected from the group consisting of: hydrogenolysis, pyrolysis, base hydrolysis, and a hydrodeoxygenation reaction.

5. The process of claim 1, further comprising, prior to step (e), upgrading the solvent product stream comprising the phenolic solvent in step (d), and wherein the phenolic solvent in step (e) is at least a portion of the upgraded phenolic solvent.

6. The process of claim 1, further comprising recycling the aqueous recycle stream back to the digestion vessel in step (b).

7. The process of claim 1, further comprising, prior to step (e), separating the solids from the solvent product stream of step (d).

8. The process of claim 1, wherein step (d) further comprises contacting the solid product stream with an organic solvent and water.

9. The process of claim 8, wherein water and organic solvent are separated from the solvent product stream in step (d), and further comprising recycling the water and organic solvent to step (d).

10. The process of claim 1, wherein the water-immiscible organic phase in step (e) further comprises the organic solvent used in step (d).

* * * * *